(12) United States Patent
Coppens et al.

(10) Patent No.: US 6,171,983 B1
(45) Date of Patent: Jan. 9, 2001

(54) FLUROALIPHATIC DIMER ACID DERIVATIVES AND USE THEREOF

(75) Inventors: Dirk M. Coppens, Antwerp (BE); Richard J. Grant, Maplewood, MN (US)

(73) Assignee: 3M Innovative Properties Company, St. Paul, MN (US)

(*) Notice: Under 35 U.S.C. 154(b), the term of this patent shall be extended for 0 days.

(21) Appl. No.: 09/391,540

(22) Filed: Sep. 8, 1999

Related U.S. Application Data

(63) Continuation of application No. 08/193,355, filed on Feb. 3, 1994, now abandoned, which is a continuation of application No. 07/791,480, filed on Nov. 12, 1991, now abandoned.

(51) Int. Cl.$^7$ .................................. C14C 9/00; B32B 5/02
(52) U.S. Cl. .......................... 442/82; 106/2; 252/8.57; 252/8.62; 427/393.4; 428/151; 428/537.5; 428/540; 442/79; 442/88; 442/92
(58) Field of Search .............. 106/2; 252/8.57; 252/8.62; 427/393.4; 428/151, 421, 422, 537.5, 540, 904; 442/79, 82, 88, 92

(56) References Cited

U.S. PATENT DOCUMENTS

| | | | |
|---|---|---|---|
| Re. 30,337 | 7/1980 | Loudas | 252/8.75 |
| 2,666,797 | 1/1954 | Husted et al. | 260/633 |
| 2,803,656 | 8/1957 | Ahlbrecht et al. | 260/556 |
| 2,809,990 | 10/1957 | Brown | 260/534 |
| 2,915,554 | 12/1959 | Ahlbrecht et al. | 260/556 |
| 2,951,051 | 8/1960 | Tiers | 260/23 |
| 3,462,296 | 8/1969 | Raynolds et al. | 117/161 |
| 3,484,281 | 12/1969 | Guenther et al. | 117/121 |
| 3,816,167 | 6/1974 | Schultz et al. | 117/138.8 F |
| 3,923,715 | 12/1975 | Dettre et al. | 260/29.6 R |
| 3,944,527 | 3/1976 | McCown | 260/79.7 |
| 4,024,178 | 5/1977 | Landucci | 260/472 |
| 4,035,506 | 7/1977 | Lucas et al. | 424/303 |
| 4,043,964 | 8/1977 | Sherman et al. | 260/29.6 F |
| 4,107,055 | 8/1978 | Sukornick et al. | 252/8.6 |
| 4,190,545 | 2/1980 | Marshall et al. | 252/8.75 |
| 4,215,205 | 7/1980 | Landucci | 525/331 |
| 4,264,484 | 4/1981 | Patel | 260/29.6 F |
| 4,325,857 | 4/1982 | Champaneria et al. | 523/412 |
| 4,340,749 | 7/1982 | Patel | 560/182 |
| 4,388,372 | 6/1983 | Champaneria et al. | 523/409 |
| 4,426,476 | 1/1984 | Chang | 524/288 |
| 4,539,006 * | 9/1985 | Langford | 8/94.1 R |
| 4,709,074 | 11/1987 | Bathelt et al. | 560/33 |
| 4,778,915 | 10/1988 | Lina et al. | 560/29 |
| 4,782,175 | 11/1988 | Wehowsky et al. | 560/26 |
| 4,898,981 | 2/1990 | Falk et al. | 568/28 |
| 4,920,190 | 4/1990 | Lina et al. | 526/288 |

FOREIGN PATENT DOCUMENTS

| | | | |
|---|---|---|---|
| 0 140 525 | 5/1985 | (EP) | C14C/9/00 |
| 999795 | 7/1965 | (GB) . | |
| 56-49081 | 5/1981 | (JP) | D60M/15/38 |

OTHER PUBLICATIONS

Leonard, Edward C., "The Dimer Acids", Humko Sheffield-Chemicals, Memphis, TN, pp. 1, 4, and 5, 1975.*

Kirk–Othmer, "Encyclopedia of Chemical Technology", John Wiley & Sons, Third Ed., vol. 7, pp. 768–782, 1979.*

Leonard, "Structure and Properties of Dimer Acids," The Dimer Acids, Hunko Sherfield Chemicals, Memphis, TN, pp. 1–17, (1975).

Kirk–Othmer, Encyclopedia of Chemical Technology, Wiley & Sons, Third Ed., vol. 4, "Carboxylic Acids," pp. 814–820, (1978).

Banks, "Organoflourine Chemicals and their Industrial Applications," pp. 226–230 (Ellis Harwood, Ltd., West Sussex, England, (1979).

Kirk–Othmer, Encyclopedia of Chemical Technology, Wiley & Sons, Third Ed., vol. 13, "Organic Isocyanates," pp. 789–793, (1981).

Schlosser, "Leather Properties of Organofluorine Compounds and their Applications in the Leather Industry,"Professional Magazine for Chemistry and Technology of Leather Manufacuturing Information Bulletin of the Association for Tanning Chemistry and Technology Inc., pp. 149–153 (1990).

* cited by examiner

*Primary Examiner*—D. S. Nakarani
(74) *Attorney, Agent, or Firm*—Lucy C. Weiss

(57) ABSTRACT

This invention relates to fluorochemical compositions, their preparation and their use as water- and oil-repellents, and substrates treated therewith. The fluorochemical composition comprises a mixture of fluorochemical compounds and/or polymers, each component having at least two fluoroaliphatic groups and a large hydrocarbon moiety such as derived from dimer acids, and the polymer having at least one fluoroaliphatic group and a plurality of said hydrocarbon moiety.

17 Claims, No Drawings

FLUROALIPHATIC DIMER ACID DERIVATIVES AND USE THEREOF

This is a continuation of application Ser. No. 08/193,355 filed Feb. 3, 1994, now abandoned, which was a continuation of application Ser. No. 07/791,480 filed on Nov. 12, 1991, now abandoned.

FIELD OF THE INVENTION

This invention relates to fluorochemical compositions comprising fluoroaliphatic dimer acid derivatives, their preparation, their use as water and oil repellents in treating substrates, such as leather, textiles and paper, and to the resulting treated substrates.

BACKGROUND OF THE INVENTION

It is common to treat the surfaces of leather, textiles, and other substrates to impart added desirable properties thereto, such as oil and water repellency and resistance to dry or oily soil. A number of fluorochemical compositions have been proposed for such treatment and several are commercially used for that purpose, such as those sold under the tradename "Scotchgard." Various patents and publications disclose a variety of such compositions for various uses, e.g. U.S. Pat. Nos. 3,462,296 (Raynolds et al.), 3,484,281 (Guenthner et al.), 3,816,167 (Schultz et al.), 3,944,527 (McCown), 4,024,178 (Landucci), 4,190,545 (Marshall et al.), 4,215,205 (Landucci) and 4,426,476 (Chang), Japanese published patent application (Kokai) No. 81-49081, and Banks, R. E., Ed., "Organofluorine Chemicals and their Industrial Applications," pages 226–230 (Ellis Harwood, Ltd., West Sussex, England, 1979). Also various patents disclose carpet treating compositions containing, inter alia, various fluorochemicals, e.g. U.S. Pat. Nos. 3,923,715 (Dettre et al.), 4,043,964 (Sherman et al.), 4,107,055 (Sukornick et al.), 4,264,484 (Patel), Re 30,337 (Loudas), 4,388,372 (Champaneria) and 4,325,857 (Champaneria). Also various patents and publications disclose the use of fluorochemical compositions on leather, e.g., U.S. Pat. Nos. 4,920,190 (Lina et al.), 4,782,175, (Wehowsky et al.), 4,778,915 (Lina et al), 4,539,006 (Langford), 3,923,715 (Dettre et al.), 4,709,074 (Bathelt et al.) and L. Schlösser "Eigenschaften fluororganischer Verbindungen und ihre Anwendung auf dem Ledergebiet," DAS LEDER, 41 Jahrgang August 1990, pages 149–153.

U.S. Pat. No. 3,923,715 (Dettre et al.) describes an aqueous dispersion containing at least 5 weight percent of a perfluoroalkyl ester made from a fluorinated alcohol and a mono- or polycarboxylic acid which contains 3 to 30 carbon atoms. The dispersion is applied to textile fibers in order to insure dry soil resistance and non-flame propagating characteristics.

U.S. Pat. No. 4,426,476 (Chang et al.) relates to a textile treatment composition containing water-insoluble fluoroaliphatic radical and aliphatic chlorine-containing ester and water-insoluble fluoroaliphatic radical-containing polymer. The ester is prepared by reacting a fluoroaliphatic chlorine-containing alcohol with a mono or polycarboxylic acid. The mono or polycarboxylic acids include acids up to 18 carbon atoms e.g. decanoic acid, tridecanedioic acid, linoleic acid.

U.S. Pat. No. 4,539,006 (Langford) relates to a composition useful for treating leather, textiles and cellulosic materials to impart water- and oil-repellency thereto. The composition contains a fluorochemical compound having a fluoroaliphatic moiety, an aliphatic moiety and an organic group which connects the fluoroaliphatic moiety and the aliphatic moiety. The composition can be prepared by, inter alia, reacting a fluoroaliphatic alcohol with a fatty acid. Useful acids contain 5 to 36 carbon atoms. Representative examples of fatty acids are linseed fatty acid, linolenic acid, oleostearic acid, ricinoleic acid, oleic acid, linoleic acid, sorbic acid, and dimer acids. The fatty acids have at least one to three unsaturated sites, and more if available. In Example 11 of this patent, the dimer acids are reacted with a perfluoroaliphatic alcohol in a ratio of 0.5 equivalent dimer acid to 0.25 equivalent alcohol [thus, the acid is not fully esterified].

Although the above-mentioned fluorochemical compositions are useful to various degrees in treating various substrates such as textile, carpet, leather, and paper, and many are commercial products, some are ineffective under normal use conditions that impart abrasive wear to the treated substrate, some provide insufficient oil or water repellency on the treated substrates, and some require high (and therefore economically undesirable) application treatment rates to obtain sufficient oil or water repellency on the treated substrates. Some fluorochemical compositions have an adverse effect on the appearance and feel or "hand" of the treated substrates.

SUMMARY OF THE INVENTION

The present invention provides, in one aspect, a fluorochemical composition comprising a mixture of normally solid, fluorochemical compounds and/or polymers each compound having at least two fluoroaliphatic groups and a large (at least 30-carbon) hydrocarbon or aliphatic moiety and the polymers having at least one fluoroaliphatic group and a plurality of the large hydrocarbon moiety. Each said fluoroaliphatic group is connected, linked, or bonded to such a hydrocarbon moiety by an organic moiety. A preferred fluorochemical composition comprises a mixture of fluoroaliphatic esters of dimer acids.

Unless otherwise indicated herein, the term "dimer acids" is used herein in its common usage to mean polymerized fatty acids products of relatively high molecular weight made up of mixtures comprising various ratios of a variety of large or relatively high molecular weight substituted cyclohexenecarboxylic acids, predominately the 36-carbon dibasic acid (dimer acid) and the 54-carbon tribasic acid (trimer acid)—see Leonard, Edward C., "The Dimer Acids," Humko Sheffield Chemical, Memphis, Tn., 1975, p. 1,4,5, and Kirk-Othmer, "Encyclopedia of Chemical Technology, John Wiley & Sons, Third Ed., Vol. 7, 1979, p. 768–770.

The fluorochemical composition of this invention has a low acid value or number (which can be measured by the method of AOCSTe 1A-64), e.g., less than about 10 or 20 and even essentially zero. Thus, in the case of the preferred fluorochemical composition comprising a mixture of fluoroaliphatic diesters and/or triesters of diner acids, such acids are essentially fully esterified and the resulting esters are thus carboxyl-free and neutral or essentially neutral, in contrast to half-esters which would be acidic due to the presence of non-esterified carboxyl functionality.

In another aspect, this invention provides processes for preparing the fluorochemical compositions by reacting diner acids with fluoroaliphatic alcohol or derivatives thereof or by reacting dimer diamines with fluoroaliphatic carboxylic acid or fluoroaliphatic alcohol derivatives. In some of these preparations, a third reactant is included, namely, polyisocyanate, polyamine, or polyol, the resulting reaction product comprising polymers having a plurality of the fluoroaliphatic groups and a plurality of the large hydrocarbon moieties. The preferred fluorochemical compositions can be prepared, for example, by fully esterifying dimer acids (such as those sold under the trademark "Pripol" which contain about 25 to 98 weight percent dimer acid and the balance being trimer acid) with fluoroaliphatic alcohol (such as an N-alkyl perfluoroalkylsulfonamidoalkyl alcohol, sometimes named as an N-alkanol perfluoroalkanesulfonamide, e.g., $C_8F_{17}SO_2N(CH_3)CH_2CH_2OH$).

In another aspect of the invention, the fluorochemical compositions are used to impart a desirable combination of surface properties to various substrates, such as fibrous substrates, e.g, textiles, carpets, paper, and leather, and siliceous substrates, e.g., ceramic tile, concrete, stone, and masonry. Said surface properties include a high degree of oil and water repellency and retention of the oil and water repellency when the treated substrates are subjected to abrasion such as that encountered in the normal use of said substrates. These properties can be obtained by contacting the surfaces of the substrates with the fluorochemical composition at low application treatment rates, the fluorochemical compositions having minimal, if any, adverse effect on the appearance and feel or "hand" of the treated substrates. The fluorochemical compositions according to this invention can be applied as a liquid treating medium in the form of an aqueous dispersion or emulsion of the fluorochemical (or fluoroaliphatic-hydrocarbon) compounds and/or polymers or of a solution thereof in an organic solvent. The aqueous dispersions are preferred from an environmental standpoint. Application of the fluorochemical composition onto the substrate can be done, for example, by spraying, padding, roll coating, brushing or exhausting the composition onto the substrate and drying the treated substrate.

DETAILED DESCRIPTION OF THE INVENTION

A class of fluorochemical compositions of this invention is that where the compositions comprise a mixture of fluoroaliphatic-hydrocarbon compounds represented by the formula:

$$(R_f\!-\!L\!-\!P)_n A \qquad\qquad I$$

wherein:
$R_f$ is a fluoroaliphatic group, such as $C_8F_{17}$—;
L is a linkage, such as —$SO_2N(CH_3)CH_2CH_2$— or —$CH_2CH_2$—;
P is a catenary, divalent heteroatom-containing carbonyl moiety, preferably —C(O)O—;
A is the above-described large hydrocarbon moiety, such as the divalent aliphatic-substituted cyclohexene-based moiety:

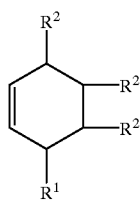

where $R^1$ and one $R^2$ are alkyl, e.g., —$(CH_2)_4CH_3$, and the other two $R^2$s are alkylene, e.g. —$CH_2$—$_8$, or alkyenylene, e.g. —$CH=CH(CH_2)_{4\ or\ 8}$, and n is an average number of 2 to 10, preferably 2 or 3.

Another class of fluoroaliphatic compositions of this invention is that where the compositions comprise a mixture of fluoroaliphatic-hydrocarbon substances, such as polymers, represented by the formula:

$$[(R_f\!-\!L\!-\!P)_{n'}\!-\!A\!-\!P]_m Z \qquad\qquad II$$

wherein:
$R_f$, L, P, and A are as defined for formula I;
Z is a mono- or poly-valent radical of hydrocarbon or fluorocarbon nature, such as the hydroxyl-free residue of an alcohol, e.g., 2-ethylhexanol or ethylene glycol, or the amino-free residue of an amine, e.g. butylamine or ethylene diamine;
n' is an average number of 1 to 10; and
m is an integer of 1 to 5.

In the present invention, the fluoroaliphatic group, such as $R_f$ in formulas I and II, is a stable, inert, nonpolar, preferably saturated, monovalent moiety which is both oleophobic and hydrophobic, preferably contains at least about 3 carbon atoms, more preferably 3 to about 20 carbon atoms, and most preferably about 6 to about 12 carbon atoms, can be straight chain, branched chain, cyclic groups or combinations thereof, is preferably free of polymerizable olefinic unsaturation, and can optionally contain one or more catenary heteroatoms such as oxygen, divalent or hexavalent sulfur, and nitrogen. It is preferred that each fluoroaliphatic group contains about 40% to about 78% fluorine by weight, more preferably about 50% to about 78% fluorine by weight. The terminal portion of the fluoroaliphatic group preferably is a fully-fluorinated terminal group. This terminal group preferably contains at least 7 fluorine atoms, e.g., $CF_3CF_2CF_2$—, $(CF_3)_2CF$—, —$CF_2SF_5$, or the like. Perfluorinated aliphatic groups, for example, those of the formula $C_xF_{(2x+1)}$ where x is 6 to 12, are the most preferred embodiments of the fluoroaliphatic group.

The linkage L in formulas I and II can be a covalent bond, a heteroatom (e.g., 0 or S), or an organic moiety. The linking organic moiety can contain 1 to about 20 carbon atoms, and optionally contains oxygen-, nitrogen-, or sulfur-containing groups or a combination thereof, and is preferably free of active hydrogen atoms. Examples of L structures include straight chain, branched chain, or cyclic alkylene, arylene, aralkylene, oxy, thio, sulfonyl, sulfinyl, imino, sulfonamido, carboxamido, carbonyloxy, urethanylene (—NHC(O)O—), ureylene, and combinations thereof such as sulfonamidoalkylene. Preferred linking groups, L, can be selected according to ease of preparation and commercial availability. Below is a representative list of suitable organic L groups. For the purposes of this list, each k is independently an integer from 1 to about 20, g is an integer from 0 to about 10, h is an integer from 1 to about 20, R' is hydrogen, phenyl, or an alkyl of 1 to about 4 carbon atoms (and is preferably methyl), and R' is alkyl of 1 to about 20 carbon atoms.

—$SO_2N(R')(CH_2)_k$—

$CON(R')(CH_2)_k$—

$(CH_2)_k$—

—$CH_2CH(OH)CH_2$—

$CH_2CH(OR'')CH_2$—

$CH_2$—$_k S$—

—$(CH_2)_k O(CH_2)_k$—

—$(CH_2)_k S(CH_2)_k$—

—$(CH_2)_k (OCH_2CH_2)_k$—

—$(CH_2)_k SO_2(CH_2)_k$—

—SO$_2$N(R') (CH$_2$)$_k$O(CH$_2$CH$_2$)$_k$—

—SO$_2$N(R')CH$_2$CH(OH)CH$_2$—

—(CH$_2$)$_k$SO$_2$N(R') (CH$_2$)$_k$—

—(CH$_2$)$_k$SO$_2$—

—OC$_6$H$_4$CH$_2$—

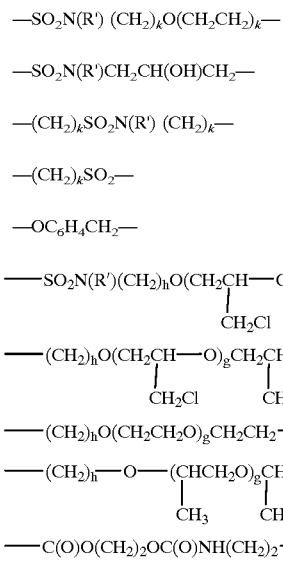

L is preferably alkylene, sulfonamido, or sulfonamidoalkylene.

The aforementioned large hydrocarbon moiety, such as A in formulas I and II, is a radical preferably having at least 30 carbon atoms. The chain in the radical may be straight, branched, or cyclic. The radical is at least divalent, and preferably trivalent, and most preferably is the carboxyl-free hydrocarbon portion of polymerized fatty acids, i.e., dimer and trimer acids and modifications thereof such as the amine analogs thereof. Such dimer acids are described, for example, in *The Dimer Acids,* Edward C. Leonard, ed., Humko Sheffield Chemical, Memphis, Tn. 1975, pp 1–17. In a preferred embodiment of the invention, the large hydrocarbon moiety has 30 to 170 carbon atoms and comprises a monocycloaliphatic moiety with 6 ring carbon atoms or a bicycloaliphatic moiety with 10 ring carbon atoms, A preferably having 34 to 51 carbon atoms.

The organic linking group P can have a wide variety of structures but where the compositions are to be used to impart repellency, it, like L, is preferably free of moieties, particular hydrophilic groups, such as acid functional groups and salts thereof, e.g., —COOH and —COONa, polyoxyethylene, polyethyleneimine, and aliphatic hydroxyl groups, which would interfere with the ability of the fluorochemical composition to impart the desired oil and water repellency to the substrate treated therewith in accordance with this invention. Bearing in mind the above-described function of the linking groups and constraints thereon, P can comprise such representative moieties as aliphatic moieties, e.g., —CH$_2$—, —CH$_2$CH$_2$—, —CH=CH—, and cyclohexylene, and aromatic moieties, e.g. phenylene, and combinations thereof, e.g. methylene di-phenylene and tolylene. P is preferably selected from hetero atom-containing moieties, e.g., carbonyloxy (—$\overset{\overset{O}{\|}}{C}$O—), carbonamido (—$\overset{\overset{O}{\|}}{C}$NH—), carbamato (—O$\overset{\overset{O}{\|}}{C}$NH—), thiocarbonyl (—$\overset{\overset{O}{\|}}{C}$S—), ureylene (—NH$\overset{\overset{O}{\|}}{C}$NH—), and —O$\overset{\overset{O}{\|}}{C}$NH—T—NH$\overset{\overset{O}{\|}}{C}$— where T represents the residue from a diisocyanate and may be (1) an aliphatic or cycloaliphatic group, for example, the residue of trimethylhexamethylene diisocyanate or the residue of methylene bis(4-cyclohexylisocyanate) or (2) an aromatic group, for example, the residue of toluene diisocyanate. As used herein, the term "residue from a diisocyanate" means the diisocyanate minus its —NCO moieties. However, it should be noted that P for a specific fluorochemical composition useful in this invention will be dictated by the ease of preparation of such a composition and the availability of the necessary precursors thereof.

The moiety Z is a mono- or multivalent radical, and can be of hydrocarbon or fluorocarbon nature, such as a saturated aliphatic or fluoroaliphatic radical, e.g., said R$_f$ or R$_f$—L, with, for example, up to 18 carbon atoms. Representative examples of Z are the hydrocarbon or fluorocarbon residues of 2-ethylhexanol, stearyl alcohol, ethylene glycol, trimethylolpropane, pentaerythritol, butylamine, stearylamine, ethylenediamine, N,N-bis(2hydroxyethyl)perfluorooctylsulfonamide, i.e., the alcohol or amine without the hydroxyl or amino group.

Representative reaction schemes suitable for preparing the fluoroaliphatic-hydrocarbon compounds or polymers of this invention include, but are not limited to, the following.

(1) Esterifying a fluoroaliphatic alcohol with dimer acids to produce fluoroaliphatic-hydrocarbon ester.

The scheme for such reaction is as follows where n is 2–3.

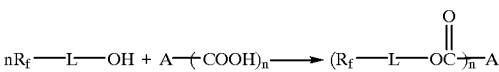

(2) (i) Reacting fluoroaliphatic alcohol with diisocyanate to produce fluoroaliphatic isocyanate-terminated urethane and (ii) reacting the latter with dimer acids to produce fluoroaliphatic-hydrocarbon urethane-amide.

The scheme for such preparation is as follows, where n is 2–3.

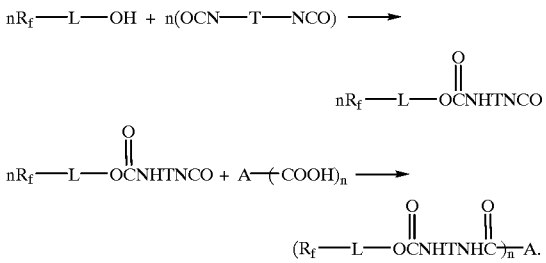

(3) Reacting fluoroaliphatic alcohol with dimer acids and hydrocarbon polyhydric alcohol.

The scheme for such esterification reaction is as follows, where n' is 1–10, and m is 1–5 .

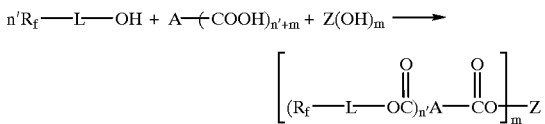

(4) (i) Reacting fluoroaliphatic alcohol and polyhydric alcohol with diisocyanate to produce isocyanate-terminated urethanes, and (ii) reacting the latter with dimer acids to produce fluoroaliphatic-hydrocarbon urethane-amide.

The scheme for such preparation is as follows, where m is 1–5, n' is 1–10, and k is about 1–5.

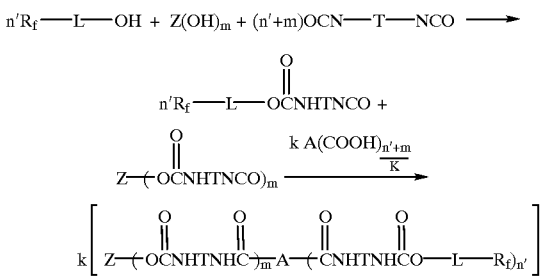

(5) Reacting fluoroaliphatic alcohol with dimer acids and polyhydric fluoroaliphatic alcohol to produce fluoroaliphatic-hydrocarbon ester.

The scheme for such reaction is as follows, where n' is 1–10, and m is 1–5.

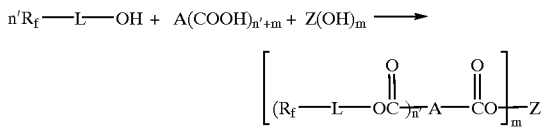

with Z containing at least one $R_f$ group.

(6) (i) Reacting fluoroaliphatic alcohol with diisocyanate to produce fluoroaliphatic isocyanate-terminated urethane and (ii) reacting the latter with primary amine analog of dimer acids to produce fluoroaliphatic-hydrocarbon urethane-urea.

The scheme for such reaction is as follows, where n is 2–3.

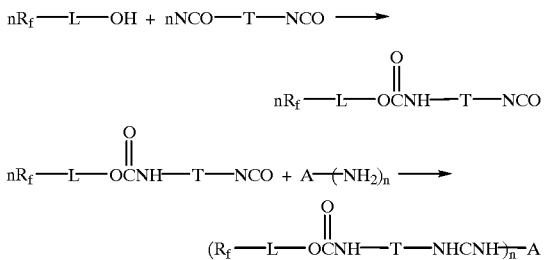

(7) Reacting fluoroaliphatic acid with primary amine analog of dimer acids to produce fluoroaliphatic-hydrocarbon amide.

The scheme for such reaction is as follows, where n is 2–3.

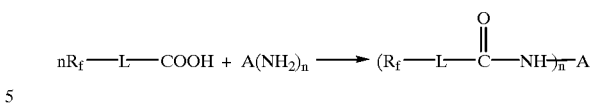

Alternatively, in the above schemes, the fluoroaliphatic alcohols can be replaced by fluoroaliphatic amines or fluoroaliphatic thiols or in the appropriate cases by fluoroaliphatic carboxylic acids.

Because of the nature of the starting materials and intermediates shown in the above schemes, and the reactions, the fluorochemical compositions of this invention will generally be mixtures of isomers and homologs. The fluoroaliphatic reactants are chemically combined with the co-reactants through the condensation of hydroxyl groups and carboxyl groups to form ester linkages, through the condensation of amino groups and carboxyl groups to form amide linkages, and through the condensation of thiol groups with carboxyl groups to form thiocarbonyl linkages, through the condensation of hydroxyl groups with isocyanate groups to form urethane linkages, through the condensation of carboxyl groups with isocyanate groups to form urea linkages, through the condensation of thiols with isocyanates to form thiourea linkages. These reactions of the fluoroaliphatic reactants with the co-reactants are carried out in a manner similar to that conventionally employed with nonfluorinated reactants, for example as described in Kirk-Othmer, "Encyclopedia of Chemical Technology, John Wiley & Sons, Third Ed., Vol. 4, 1981, *Carboxylic Acids,* p. 814–829. and Vol. 13, 1981, *Organic Isocyanates,* p. 789–793.

Monofunctional fluoroaliphatic alcohols useful in preparing the fluorochemical compositions of this invention include the N-alkanol perfluoroalkylsulfonamides described in U.S. Pat. No. 2,803,656 (Ahlbrecht et al.), which have the general formula $R_fSO_2N(R)R_1CH_2OH$ wherein $R_f$ is a perfluoroalkyl group (including perfluorocycloalkyl) having 4 to 10 carbon atoms, $R_1$ is an alkylene radical having 1 to 12 carbon atoms, and R is a hydrogen atom or an alkyl group containing 1 to 4 carbon atoms and is preferably methyl. These monofunctional alcohols can be prepared by reactions of an acetate ester of halohydrin with a sodium or potassium salt of the corresponding perfluoroalkylsulfonamide.

Illustrative fluoroaliphatic alcohols include the following: N-ethyl N-(2-hydroxyethyl) perfluorooctylsulfonamide, N-propyl N-(2-hydroxyethyl) perfluorooctylsulfonamide, N-ethyl N-(2-hydroxyethyl) perfluorodecylsulfonamide, N-ethyl N-(2-hydroxyethyl) perfluorododecylsulfonamide, N-ethyl N-(2-hydroxyethyl) perfluorocyclohexylethylsulfonamide, N-propyl N-(2-hydroxyethyl) perfluorobutylcyclohexylsulfonamide, N-ethyl N-(2-hydroxyethyl) perfluoro-4-dodecylcyclohexylsulfonamide, N-ethyl N-(2-hydroxyethyl) perfluoro-2-methylcyclohexylsulfonamide, N-ethyl N-(6-hydroxyhexyl) perfluorooctylsulfonamide, N-methyl N-(11-hydroxyundecyl) perfluorooctylsulfonamide, N-methyl N-(4-hydroxybutyl) perfluorobutylsulfonamide, N-(2-hydroxyethyl) perfluorooctylsulfonamide, N-methyl N-(2-hydroxyethyl) perfluorooctylsulfonamide. Still other alcohols useful in preparing the fluorochemical compositions of the invention include the perfluoroalkyl-substituted alkanols of the formula $C_nF_{2n+1}CH_2OH$, where n is 4 to 10 (e.g., $C_4F_9CH_2OH$), described, for example, in U.S. Pat. No. 2,666,797 (Husted et al.), and of the formula $R_f(CH_2)_mOH$ where $R_f$ is a perfluoroalkyl radical having from 4 to 10 carbon atoms and m is an integer from 1 to 4 (e.g., $C_8F_{17}CH_2CH_2CH_2OH$, $C_8F_{17}CH_2CH_2CH_2CH_2OH$,

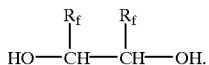

Perfluoroalkyl-substituted alkanols, e.g., $C_nF_{2n+1}$ $(C_mH_{2m-2})$OH where n is 4 to 10 and m is to 4, e.g., $C_8F_{17}CH=CHCH_2OH$, can also be used in preparing fluorochemical compositions of this invention. Further useful monofunctional alcohols include the N-[hydroxypoly-(oxyalkylene)]-perfluoroalkylsulfonamides of U.S. Pat. No. 2,915,554 (Ahlbrecht et al.), such as

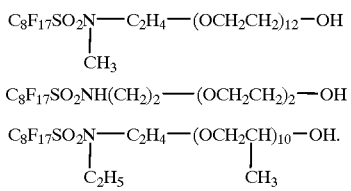

Other alcohols which can be used in preparing the fluoroaliphatic compositions of this invention are those of the formula $HO-OH_2C(CH_2SCH_2CH_2R_f)_2CH_2OH$ described in U.S. Pat. No. 4,898,981, as well as the mono alcohols also described therein.

The carboxyl-containing fluoroaliphatic reactants useful in making the fluorochemical compositions include the monofunctional perfluoroalkylsulfonamidoalkylene carboxylic acids of U.S. Pat. No. 2,809,990 (Brown), which have the general formula:

wherein:

$R_f$ is a perfluoralkyl (including perfluorocycloalkyl) group having from 4 to 10 carbon atoms, R is hydrogen or an alkyl group having from 1 to 4 carbon atoms (and is preferably methyl), and $R_2$ is an alkylene group having from 1 to 12 carbon atoms. Illustrative acids include the following:

N-ethyl N-perfluorooctylsulfonyl glycine,

N-perfluorooctylsulfonyl glycine,

N-perfluoropentylsulfonyl glycine,

N-perfluorodecylsulfonyl glycine, 3-(perfluorooctylsulfonamido) propionic acid, 11-(N-methyl N-perfluorooctylsulfonamido) undecanoic acid, 11-(N-ethyl N-perfluorooctylsulfonamido) undecanoic acid, N-ethyl N-perfluorocyclohexylsulfonyl glycine, N-ethyl N-perfluorocyclohexylethylsulfonyl glycine, N-butyl N-perfluoro-4-dodecylcyclohexylsulfonyl glycine, N-ethyl N-perfluoro-2-methylcyclohexylsulfonyl glycine, N-hexyl N-perfluorooctylsulfonyl glycine, N-ethyl N-perfluorobutylsulfonyl glycine.

Still other carboxyl-containing fluorocarbon reactants include the perfluoro-substituted aliphatic acids, described in U.S. Pat. No. 2,951,051 (Tiers), such as $C_8F_{17}CH_2CH_2CH_2CH_2COOH$, 5-perfluorobutyl pentanoic acid, and 11-perfluorooctylhendecanoic acid, as well as the unsaturated perfluoroalkane aliphatic acids, e.g. $R_fCH=CH-(CH_2)_7CH_2CO_2H$, also described in said U.S. Pat. No. 2,951,051, and those of the formula $R_f(CH_2CH_2S)_2C(CH_3)CH_2CH_2COOH$ described in U.S. Pat. No. 4,898,981.

The large hydrocarbon radical, such as A in formulas I and II, is most preferably derived from polymerized fatty acids (or dimer acids). Polymerized fatty acids and analogs useful in the practice of this invention contain at least 32 carbon atoms. It is preferred that the polymerized fatty acid is a trimer acid with 54 carbon atoms, or a dimer acid with 36 carbon atoms, or mixtures of trimer acids with dimer acids with 36 to 54 carbon atoms, such as those commercially available, for example, as Pripol™ 1009, Pripol™ 1022, Pripol™ 1040, Pripol™ 1046, Pripol™ 1049, Unidyme™ 14, Unidyme™ 18, Unidyme™ 22, Unidyme™ 24, Unidyme™ 60, Hystrene™ 3695, Hystrene™ 3680, Hystrene™ 3675, Hystrene™ 3676C, and Hystrene™ 5460, and the primary amine analogs of the polymerized fatty acids, available, for example, as Kemamine™ DP-3695 and Kemamine™ DP-3680, and their derivatives such as dimer acid diisocyanates. The polymerized fatty acids can be prepared from fatty acids with at least 16 carbon atoms, e.g., palmitoleic acid, linoleic acid, linolenic acid, oleic acid, rinoleic acid, gadoleic acid, eracic acid or mixtures thereof.

Diisocyanates useful in preparing fluorochemical compositions of this invention can be selected from aromatic, aliphatic and cycloaliphatic diisocyanates. Representative examples of diisocyanates are, for example, trimethylhexamethylene diisocyanate, methylene-bis (4-cyclohexyl isocyanate), and toluene diisocyanate.

Solvents that are suitable for dissolving the fluoroaliphatic-hydrocarbon compounds and polymers include chlorinated hydrocarbons, isoparaffinic hydrocarbons, alcohols, e.g., isopropyl alcohol, esters, ketones, e.g., methyl isobutyl ketone, and mixtures thereof. Usually, the solvent solutions will contain 0.1 to 10% or even up to 50% by weight non-volatile solids.

Preferably, aqueous dispersions of the fluoroaliphatic-hydrocarbon compounds and polymers are used to treat the substrate. Usually they will be concentrates diluted with water to a non-volatile solids content of 0.1 to 30%, preferably 1 to 10%, by weight.

The amount of the fluorochemical composition applied to a substrate in accordance with this invention is chosen so that sufficiently high or desirable water and oil repellencies are imparted to the substrate surface, said amount usually being such that 0.01% to 5% by weight, preferably 0.05 to 2% by weight, of fluorine is present on the treated substrate. The amount which is sufficient to impart desired repellency can be determined empirically and can be increased as necessary or desired.

To prepare the aqueous dispersions, the active fluoroaliphatic-hydrocarbon products, together with cationic or anionic and, if appropriate, nonionic dispersing and/or emulsifying or surfactant agents and, if appropriate, other auxiliaries and solvents, are vigorously dispersed in water, a relatively large amount of energy being supplied. To facilitate the preparation of the dispersion, the fluoroaliphatic-hydrocarbon product may be dissolved first in solvent or mixture of solvents, and the dispersion is advantageously carried out in two separate steps, predispersion being carried out first, followed by fine dispersion. Predispersion can also be carried out by using high shearing forces, for example by using a high-speed stirrer, such as a dispersing machine of the Ultraturax™ type, and the predispersion thereby obtained is then subjected, for example, to ultrasonic treatment or treatment in a high pressure homogenizer. After this treatment, the particle size in the dispersion generally will be equal to or less than 1 μm to the extent of more than 80%, preferably to the extent of more than 95%. Generally, the aqueous dispersion as a concentrate contains about 5 to 50% by weight of active composition (fluoroaliphatic-hydrocarbon products), about 0.5 to 15% by weight of one or more dispersing and/or emulsifying agents, and about 0 to 30% by weight of a solvent or solvent mixture, the remainder being water. Solventless dispersions can be prepared by removing the solvent by distillation.

Mixtures of water-insoluble solvents with water-soluble solvents can be employed as the solvent for preparation of the dispersion, the amount of the water-insoluble solvent in most cases being greater than the water-soluble solvent. Suitable water-soluble solvents are, for example, mono- or di-alcohols, lower ketones, polyglycol esters, and polyglycol ethers, or mixtures of such solvents. Examples of water-insoluble solvents are esters, ethers, and higher ketones. Low-boiling solvent portions can be removed by, for example, distillation, at a later time if desired. Preferred water-insoluble solvents are esters or ketones, such as ethyl acetate, butyl acetate, and methyl ethyl ketone.

For the treatment of some substrates, it may be advantageous to incorporate into the fluorochemical compositions of this invention, such as the above-described dispersions, one or more other substances such as fluorochemicals or silicones, to increase repellency properties and the durability thereof and to aid in the application of the fluorochemical composition to the substrate to be treated therewith. Also, various adjuvants may be incorporated into the fluorochemical compositions of this invention to impart special properties thereto, for example, hydrocarbon extenders can be added for soil resistance or water repellency. In treating textile substrates such as apparel fabrics, known oil and water repellent fluorochemical substances, such as the blend of fluoroaliphatic carbodiimide and fluoroaliphatic radical-containing polymer (e.g., copolymers of acrylate esters and methacrylate esters of perfluoroalkanesulfonamido alkanols described in said U.S. Pat. No. 4,215,205), may be incorporated in the fluorochemical compositions along with the fluoroaliphatic-hydrocarbon compounds or polymers described herein (such as that of Example 1, infra). Commercially available examples of such other fluorochemical substances are sold under the "Scotchgard" trademark.

In the following nonlimiting examples, objects and advantages of this invention are illustrated, where all parts and percentages are by weight unless otherwise noted. In the examples where the fluorochemical compositions of the invention are applied to various substrates, the following test methods are used for evaluation.

Spray Rating

The spray rating (SR) of a treated substrate is a value indicative of the dynamic repellency of the treated substrate to water that impinges on the treated substrate, such as encountered by apparel in a rainstorm. The rating is measured by Standard Test Number 22, published in the 1977 Technical Manual and Yearbook of the American Association of Textile Chemists and Colorists (AATCC), and is expressed in terms of the "spray rating" of the tested substrate. The spray rating is obtained by spraying water on the substrate and is measured using a 0 to 100 scale where 100 is the highest possible rating. In general, a spray rating of 70 or greater is desirable.

Oil Repellency

The oil repellency (OR) of a treated substrate is measured by the American Association of Textile Chemists and Colorists (AATCC) Standard Test Method No. 118-1983, which test is based on the resistance of treated substrate to penetration by oils of varying surface tensions. Treated substrates resistant only to Nujol™ mineral oil (the least penetrating of the test oils) are given a rating of 1, whereas treated substrates resistant to heptane (the most penetrating of the test oils) are given a rating of 8. Other intermediate values are determined by use of other pure oils or mixtures of oils, as shown in the following table.

| AATCC Oil Repellency Rating Number | Composition |
|---|---|
| 1 | Nujol ™ mineral oil |
| 2 | 65:35 Nujol ™:hexadecane by volume at 70° F. (21° C.) |
| 3 | n-hexadecane |
| 4 | n-tetradecane |
| 5 | n-dodecane |
| 6 | n-decane |
| 7 | n-octane |
| 8 | n-heptane |

The rated oil repellency corresponds to the most penetrating oil (or mixture of oils) which does not penetrate or wet the tested substrate after 30 seconds contact time. Higher numbers indicate better oil repellency. In general, an oil repellency of 3 or greater is desirable.

Water Repellency

The water repellency (WR) of a treated substrate is measured using a water-isopropyl alcohol test liquid, and is expressed in terms of the "WR" rating of the treated substrate. Treated substrates which are penetrated by or resistant only to a 100% water-0% isopropyl alcohol liquid, the least penetrating of the test liquids, are given a rating of 0, whereas treated substrates resistant to a 0% water-100% isopropyl alcohol test liquid, the most penetrating of the test mixtures, are given a rating of 10. Other intermediate values are determined by use of other water-isopropyl alcohol test liquids, in which the percentage amounts of water and isopropyl alcohol are each multiples of 10. The WR rating corresponds to the most penetrating test liquid which does not penetrate or wet the substrate surface after 15 seconds contact. In general, a WR rating of 3 or greater is desirable.

Bundesmann "Rain-Repellency"

In the Bundesmann test method (DIN 53888), the test fabric sample is subjected to a simulated rainfall, while the sample is moved in the rainfall. During the whole test, the back of the sample is rubbed. This test is intended to siulate actual use of fabrics in the rain. The following measurement ratings are made:

The amount of water that penetrated the fabric;

The appearance of the surface: best rating is 5 (no water remains on the surface), worst rating is 1 (complete surface wetting).

Bally Penetrometer

For the testing of shoe leather uppers for water repellency, a Bally penetrometer Model 5023 (a standardized dynamic testing machine for shoe upper leather) was used. In this test, the test piece was alternatively buckled and stretched by the machine, like an upper leather in actual use, while in contact with water on one side. The values measured in this test are:

1. the time until water first penetrates from one side of the test piece of treated leather to the other (said time is, for untreated leather, typically less than 15 minutes), and 2. the weight percent increase of the test piece caused by water absorption during the test (said weight increase, for untreated leather, is typically greater than 100% after one hour).

Abraded Oil and Water Repellency

The repellency of an abraded treated substrate is measured on 5 cm×12.5 cm test pieces of treated substrate which has been abraded using 10 back and forth rubs over a 5-second period with abrasive paper ("WETORDRY - TRIM-ITE" No600C) in an AATCC crockmeter (Model CM-1) The above-described OR and WR repellency tests are performed on the abraded test pieces and the repellency ratings recorded as Abraded Oil Repellency (AOR) and Abraded Water Repellency (AWR) values.

Static Oil Absorption

Static oil absorption is a test designed to measure the degree of resistance of drum-treated leather to absorption of oil under static conditions. A 50×50 mm test piece is weighed and held upright in a beaker of Nujol™ mineral oil so that the upper edge of the piece is 6 mm below the oil surface. After a 10-minute immersion period, the test piece is removed, surface oil lightly blotted off with absorbent paper, and reweighed. Results are recorded as percent oil absorbed, using the formula:

$$\left(\frac{W2 - W1}{W1}\right) \times 100 = \%$$

Where W1 is original weight of the piece and W2 is weight of the piece after immersion.

EXAMPLE 1

A fluorochemical composition of this invention, comprising an aqueous dispersion of a mixture of fluoroaliphatic-hydrocarbon esters, was prepared as follows.

In a 2-liter, three-necked, round-bottomed flask, equipped with a mechanical stirrer, a reflux condenser fitted with a Dean-Stark water trap, temperature control, and heating mantle, were charged 500 g (0.90 mole) N-methyl-perfluorooctylsulfonamidoethyl alcohol, 250 g Pripol™ 1040 polymerized fatty acid (0.90 equivalents acid, consisting of about 25% dimer acid and 75% trimer acid), 150 g xylene, and 30 g Amberlyst™ 15 cation exchange resin. The resulting mixture was stirred and refluxed in an atmosphere of nitrogen at 144° C. for about 16 hours to complete the esterification reaction, as indicated by the amount of water given off as a by-product. The xylene was distilled off under reduced pressure, and the warm, liquid, fluoroaliphatic-hydrocarbon ester product was filtered to remove the ion exchange resin. At room temperature, the product was an amber solid. Infra-red spectroscopy and gas chromatography confirmed its ester structure and the complete esterification of the fluoroaliphatic alcohol, the product thus determined as having a structure falling within formula I, supra. A first dispersion of the product was prepared as follows.

Forty g of the fluoroaliphatic-hydrocarbon ester product was dissolved in 60 g ethylacetate and 2 g Sarcosyl™ O emulsifier. The resulting solution was heated to 60° C. Separately, 79 g de-ionized water was mixed with 13.3 g ethylene glycol and 0.75 g NH$_4$OH (32%), and the resulting mixture was also heated to 60° C. The warm ester solution was then poured into the warm water solution under vigorous stirring to form a predispersion. The pre-dispersion was then treated by ultrasonic waves for 6 minutes, forming a stable dispersion. The ethylacetate was removed under vacuum stripping. The resulting ethylacetate-free dispersion was filtered through a 25μ pore size filter bag. A stable, milky-white, anionic, aqueous fluorochemical dispersion of 30% active material, viz., neutral fluoroaliphatic-hydrocarbon ester, was obtained. (A second dispersion of the above-described fluoroaliphatic-hydrocarbon ester product was prepared by the dispersion procedure described in Example 14 below.)

EXAMPLES 2–10

Following the general procedures of Example 1 and using the fluorochemical alcohols and polymerized fatty acid precursors listed below, all in stoichiometric ratios, nine fluorochemical compositions were prepared, each comprising a dispersion of a mixture of fluoroaliphatic-hydrocarbon esters of formula I, supra.

| Ex. | Fluorochemical alcohol | Polymerized acid |
|---|---|---|
| 2 | C$_8$H$_{17}$SO$_2$N(CH$_2$CH$_3$)CH$_2$CH$_2$OH | Pripol ™ 1040 |
| 3 | C$_8$F$_{17}$SO$_2$N(CH$_3$)CH$_2$CH$_2$OCH$_2$CH—OH<br>$\quad\quad\quad\quad\quad\quad\quad\quad\quad\quad\quad\quad\quad\quad$ \|<br>$\quad\quad\quad\quad\quad\quad\quad\quad\quad\quad\quad\quad\quad\quad$ CH$_2$Cl | Pripol ™ 1040 |
| 4 | C$_8$H$_{17}$CH$_2$CH$_2$OH | Pripol ™ 1040 |
| 5 | C$_8$H$_{17}$SO$_2$N(CH$_3$)CH$_2$CH$_2$OH | Pripol ™ 1009 (98% dimer acid) |
| 6 | C$_8$H$_{17}$SO$_2$N(CH$_3$)CH$_2$CH$_2$OH | Pripol ™ 1022 (75% dimer acid, 22% trimer acid) |
| 7 | C$_8$H$_{17}$SO$_2$N(CH$_3$)CH$_2$CH$_2$OH | Pripol ™ 1046 (60% trimer acid, 40% dimer acid) |
| 8 | C$_8$H$_{17}$SO$_2$N(CH$_3$)CH$_2$CH$_2$OH | Hystrene ™ 5460 (60% trimer acid, 40% dimer acid) |
| 9 | C$_8$H$_{17}$SO$_2$N(CH$_3$)CH$_2$CH$_2$OH | Hystrene ™ 3675 (16% trimer acid, 83% dimer acid) |
| 10 | C$_8$H$_{17}$SO$_2$N(CH$_3$)CH$_2$CH$_2$OH | Unidyme ™ 60 (75% trimer acid, 25% dimer acid) |

EXAMPLE 11

Into a 500 ml three-necked, round-bottomed flask, equipped with a mechanical stirrer, condenser, thermometer, and heating mantle, were charged 53.0 g N-methylperfluorooctylsulfonamidoethyl alcohol, 20.0 g tri-methylhexamethylene diisocyanate, 90 g ethylacetate and 0.05 g stannous octoate, and the resulting mixture was heated to 75° C. and stirred for 4 hrs. 27.0 g Pripol™ 1040 was added to the mixture and the resulting mixture was stirred overnight at 75° C. 0.05 g additional stannous octoate was added and the reaction continued for 8 hours. IR spectrum of the reaction mixture showed no residual NCO absorption band. The reaction mixture was cooled to room temperature and 50 g ethylacetate added. A clear brown solution of 40% fluorochemical solids, fluoroaliphatic-hydrocarbon urethaneamido product (within the scope of Formula II, supra.), was obtained. This fluorochemical solution was dispersed as described in Example 1.

EXAMPLE 12

Into a 250 ml three-necked, round-bottomed flask, equipped with a mechanical stirrer,. a reflux condenser fitted with a Dean-Stark trap, temperature control, and heating mantle, were charged 47.3 g N-methylperfluorooctylsulfonamidoethyl alcohol (0.085 equivalents alcohol), 28.3 g Pripol™ 1040 polymerized fatty acid (0.10 eq. acid), 0.675 g trimethylolpropane (0.015 equivalents alcohol), 3.8 g Amberlyst™ 15 catalyst and 75 g xylene as solvent. The resulting mixture was stirred and refluxed in an atmosphere of nitrogen at 144° C. for about 16 hours to complete the esterification reaction, as indicated by the amount of water given off as a by-product. The xylene was distilled off under reduced pressure, and the warm liquid was filtered to remove the Amberlyst™ 15. The neutral fluoroaliphatic hydrocarbon ester product, falling within formula II, supra., as confirmed by IR and GC analyses, was then dispersed as described in Example 1.

EXAMPLE 13

In a 250 ml, three necked, round bottomed flask, equipped with a mechanical stirrer, a reflux condenser fitted with a Dean-Stark water trap, temperature control, and heating mantle, were charged 24.9 g fluorochemical diol of the formula $C_8F_{17}SO_2N(CH_2CH_2OH)_2$ (0.085 eq. alcohol), 31.5 g N-methyl-perfluorooctylsulfonamidoethyl alcohol (0.057 eq. alcohol), Pripol™ 1009 polymerized fatty acid (0.14 equivalents acid), 5 g Amberlyst™ 15 resin, 100 g xylene. The resulting mixture was stirred and refluxed in an atmosphere of nitrogen at 144° C. for about 16 hrs to complete the esterification reaction, as indicated by the amount of water given off as a by-product. The xylene was distilled off under reduced pressure, and the warm liquid product was filtered to remove the Amberlyst™ 15. At room temperature, an amber solid was obtained, viz., neutral fluoroaliphatic-hydrocarbon polyester product, with structure falling within formula II, supra., which was dispersed as follows.

Forty g of the polyester product and 1 g Tween™ 80 nonionic surfactant were dissolved in 60 g ethylacetate. The resulting solution was heated to 60° C.

Separately, 79 g de-ionized water was mixed with 13.3 g ethylene glycol and 1.0 g Siponate™ DS-10 surfactant. The resulting mixture was also heated to 60° C. The warm polyester solution was then poured into the warm water solution under vigorous stirring to form a pre-emulsion. This pre-emulsion was then treated for 6 minutes by ultrasonic waves to form a storage-stable dispersion. The ethyl acetate was removed under vacuum stripping. The dispersion was then diluted to 30% solids with water.

EXAMPLE 14

One-Hundred Fifty g ester product prepared as in Example 1 was diluted with 225 g ethyl acetate and 3.75 g Tween™ 80 surfactant. The resulting solution was heated to 60° C. Separately, 300 g de-ionized water was mixed with 50 g ethylene glycol and 3.75 g Ethoquad™ HT-25 cationic surfactant. The resulting solution was also heated to 60° C. The ethyl acetate solution was then poured into the water solution while stirring with an Ultraturax™ high speed mixer. After complete addition of the ethyl acetate solution, the stirring was continued for 2 minutes at full speed. This resulted in a preemulsion with limited stability. The pre-emulsion was then passed 2 times through a 2-step Manton Gaulin™ high-pressure homogenizer (pressure settings at 20 and 200 bar) to form the stable dispersion. The ethyl acetate was then stripped under vacuum at 60° C. and the final, stable, ethyl acetate-free, cationic dispersion was diluted to 30% solids.

EXAMPLES 15–27

The fluorochemical compositions of Examples 1–13 were applied to upholstery leather (bovine) in a bath exhaust treatment. The fluorochemical compositions were applied during the final wet production step of the leather, viz., after the standard chrome tanning, retanning, dying, and fat-liquoring steps used for processing upholstery leather. For this purpose, the fluorochemical compositions were added in an amount of 1.6% by weight of fluorochemical solids, relative to the shaved weight of the leather, to the fat-liquoring bath (which contained a liquor amounting to 200% by weight of water relative to the shaved weight of leather). The bath temperature was 50° C. and the pH 4.5 at the moment of addition of the fluorochemical composition. The exhaust process was continued for 30 minutes, afterwhich the pH was lowered to 3.5 with formic acid.

After the treated leathers were dried and finished in conventional manner, the OR, WR, SR, AOR, AWR tests were conducted on the grain side of the treated leather. The results are set forth in Table 1.

For comparison purposes, three dispersions of known fluorochemical compositions (Comparative Examples 1–3) were prepared as described below, and likewise evaluated, as Comparative Examples 4–6, and the results of their evaluation are also included in Table 1.

Comparative Example 1

As a comparative example, the product prepared in Example 1 of U.S. Pat. No. 4,539,006 was made by fully esterifying N-methylperfluorooctyl sulfonamidoethyl alcohol with linseed fatty acid. After the reaction, xylene was distilled off and the resulting fluoroaliphatic monoacid ester was dispersed using the procedure described in Example 1.

Comparative Example 2

As a second comparative example, the product prepared in Example 11 of U.S. Pat. No. 4,539,006 was made by partially esterifying N-methylperfluorooctyl sulfonamidoethyl alcohol with Pripol™ 1009 dimer acid,,the equivalent alcohol/acid ratio was ½, so only 50% esterification was possible. After the reaction the xylene was distilled off, and the resulting essentially fluorochemical half-ester product was dispersed using the procedure described in Example 1.

Comparative Example 3

As a third comparative example, the product prepared at example 8 of U.S. Pat. No. 4,264,484 was made by reacting adipic acid with the reaction product of epichlorohydrin and the fluoroaliphatic radical-containing alcohol, N-methylperfluorooctyl sulfonamidoethyl alcohol, and the resulting diester was then dispersed according to the procedure described in Example 1.

TABLE 1

Performance Test Results on Upholstery Leather

| Example Number | Fluorochemical Composition From Example No. | OR | WR | AOR | AWR | SR |
|---|---|---|---|---|---|---|
| 15 | Example 1 | 6 | 9 | 6 | 9 | 90 |
| 16 | Example 2 | 3 | 2 | 3 | 2 | 90 |
| 17 | Example 3 | 4 | 2 | 4 | 1 | 80 |
| 18 | Example 4 | 6 | 8 | 5 | 8 | 90 |
| 19 | Example 5 | 4 | 7 | 4 | 7 | 90 |
| 20 | Example 6 | 5 | 8 | 5 | 7 | 90 |
| 21 | Example 11 | 4 | 5 | 4 | 4 | 80 |
| 22 | Example 12 | 5 | 9 | 5 | 9 | 80 |
| 23 | Example 13 | 5 | 9 | 5 | 9 | 80 |
| 24 | Example 7 | 6 | 9 | 6 | 9 | 80 |
| 25 | Example 8 | 6 | 9 | 6 | 8 | 80 |
| 26 | Example 9 | 5 | 9 | 5 | 9 | 80 |
| 27 | Example 10 | 6 | 7 | 5 | 7 | 80 |
| Comparative Example 4 | Comparative Example 1 | 1 | 2 | 0 | 2 | 80 |

TABLE 1-continued

Performance Test Results on Upholstery Leather

| Example Number | Fluorochemical Composition From Example No. | OR | WR | AOR | AWR | SR |
|---|---|---|---|---|---|---|
| Comparative Example 5 | Comparative Example 2 | 2 | 3 | 1 | 2 | 70 |
| Comparative Example 4 | Comparative Example 3 | 2 | 2 | 1 | 1 | 50 |

The data of Examples 15–27 of Table 1 show that the fluorochemical compositions of this invention generally impart good to excellent repellency to leather. The OR, WR, AOR, and AWR data for Example 16 are not as high as compared to, for example, that of Example 15, but the SR value of Example 16 is excellent. And though the WR and AWR data of Example 17 are not high, the SR, OR, and AOR data are much higher than that of Comparative Example 6. The data of Example 19 is particularly noteworthy in comparison with that of Comparative Example 5, which is based on a fluorochemical half-ester rather than full ester.

EXAMPLE 28

The same application procedure of Examples 15–27 was used to apply the dispersion product made in Example 1 to white shoe leather, prepared using standard shoe leather tanning process. Performance results are set forth in Table 2, together with the results of Comparative Examples 7–12 where commercially available fluorochemical leather protector products were applied in the same manner.

TABLE 2

Performance Test Results on White Shoe Leather

| Example No. | OR | WR | AOR | AWR | SR | Static Oil Absorption |
|---|---|---|---|---|---|---|
| 28 | 6 | 9 | 5 | 7 | 80 | 3% |
| Comparative Example 7 | 2 | 2 | 2 | 2 | 70 | 16% |
| Comparative Example 8 | 1 | 2 | 1 | 2 | 70 | 4% |
| Comparative Example 9 | 2 | 3 | 0 | 2 | 70 | 3% |
| Comparative Example 10 | 1 | 4 | 0 | 2 | 90 | 6% |
| Comparative Example 11 | 0 | W* | 0 | W* | 50 | 48% |
| Comparative Example 12 | 0 | 1 | 0 | 1 | 100 | 26% |

*"W" means the substrate was wetted by the water test liquid.

The data of Table 2 show the fluorochemical composition of this invention gave excellent overall repellency and oil hold-out (static oil absorption).

EXAMPLES 29–34

The same general bath application procedure as described for Examples 15–27 was used to apply the dispersion prepared in Example 1. This product was applied to different types of leather, each prepared by a tanning, re-tanning, dying, and fat-liquoring process typical for the preparation of each leather type.

The following leather substrates were used
Example 29: Garment, wool-on, double face sheepskin, type 1
Example 30: Garment, wool on, double face sheepskin, type 2
Example 31: Garment, Nappa sheepskin
Example 32: Shoe leather; full grain type, bovine
Example 33: Shoe leather, suede, bovine
Example 34: Shoe leather, Nubuc, bovine Performance results and % fluorochemical solids on shaved weight are listed in Tables 3A and 3B.

TABLE 3A

Performance Results on a Variety of Different Leather Types

| Example No. | % Solids Applied | OR | WR | AOR | AWR | SR | Static Oil Absorption |
|---|---|---|---|---|---|---|---|
| 29 | 0.6 | 6 | 10 | 5 | 9 | 70 | — |
| 30 | 1.6 | 6 | 10 | 5 | 10 | 70 | — |
| 31 | 1.2 | 6 | 10 | 6 | 10 | 70 | 6% |
| 32 | 1.6 | 6 | 10 | 5 | 9 | 90 | 2% |
| 33 | 1.6 | 5 | 8 | 5 | 8 | 100 | 2% |
| 34 | 1.6 | 5 | 9 | 5 | 8 | 90 | 5% |

The data of Table 3A show that the fluorochemical composition of this invention can impart excellent repellency to a wide variety of leathers.

TABLE 3B

Bally Penetrator Test Results

| Example No. | Water Transfer | Absorption 2 hours | Absorption 23 hours |
|---|---|---|---|
| 32 | >2 hours | 15% | — |
| 33 | >23 hours | — | 22% |
| 34 | >2 hours | 25% | — |

The data of Table 3B show the fluorochemical composition of this invention significantly reduces the rate of water permeation and amount of water absorbed by leather treated with said composition.

EXAMPLES 35–36

The dispersion product prepared in Example 1 was applied to leather by spraying with an airless sprayer. For this application, the dispersion product was diluted to a solids content of 5% and sprayed onto the leather surface. 5.4 g of this diluted product were sprayed on a 20×30 cm leather surface. The leather specimens were dried at 60 or 95° C. In Example 35, a yellow, full-grain upholstery leather was used, and in Example 36, a brown, full-grain garment leather was used. Performance results are given in Table 4.

TABLE 4

Aqueous Spray Application On Leather

| Example No. | Dried at 60° C. | | | | | Dried at 95° C. | | | | |
|---|---|---|---|---|---|---|---|---|---|---|
| | OR | WR | AOR | AWR | SR | OR | WR | AOR | AWR | SR |
| 35 | 4 | 8 | 5 | 9 | 90 | 4 | 8 | 6 | 8 | 90 |
| 36 | 4 | 4 | 3 | 3 | 90 | 4 | 7 | 5 | 7 | 90 |

The data of Table 4 show the excellent results obtained by spraying the fluorochemical composition.

EXAMPLES 37–38

The dispersion product prepared in Example 14 was evaluated at two different application levels on a non-woven, 60/40 cellulose wood pulp/polyester substrate, having a thickness of about 50 microns and a basis weight of 45 g/m². In Example 37, 6.66 g dispersion product was diluted to 100 g with water (resulting in 0.2% solids on fibre) and in Example 38, 13.33 g dispersion product was diluted to 100 g with water (resulting in 0.4% solids on fibre). The non-woven substrate was then dipped into a treating bath of the diluted dispersion and squeezed to a wet pick up of 15%. The treated substrates were dried at 60° C. for 2 minutes. The OR and WR of the non-wovens was measured and the excellent repellency results are set forth in Table 5.

TABLE 5

Performance on Non-woven Substrates

| Example | % SOF | OR | WR |
|---------|-------|----|----|
| 37 | 0.2 | 7 | 10 |
| 38 | 0.4 | 8 | 10 |

EXAMPLE 39

The dispersion product prepared in Example 14 was used in treating a beige-dyed nylon 6, 500 g/m², tufted carpet. The treating formulation, containing 15 g/l of the dispersion product and 15 g/l of a 20% solids emulsion of a 50/50 methylmethacrylate/ethylmethacrylate copolymer, was sprayed onto the carpet at a wet pick-up level of 20%. The carpet sample was then dried and cured at 120° C. for 4 minutes. Though the treated carpet had an OR rating of only 2 (and could probably be made higher if greater pick-up level was used), it had an acceptable WR of 3.

EXAMPLE 40

Stone floor-tiles were treated with the dispersion product prepared as in Example 1. For this purpose, the dispersion product prepared was diluted to 5% solids with water and brushed onto the stone floor-tile. The stone floor-tile was dried overnight at room temperature, and showed an OR value of 7, a WR value of 10, and a SR of 100, all excellent.

EXAMPLE 41

The cationic dispersion made in Example 14 was used in combination with a blend of fluoroaliphatic carbodiimide and vinyl polymers in a textile treatment formula. For comparison, a-similar formulation, Comparative Example 13, was made without including the fluorochemical composition of Example 14. These formulations are set forth below.

TABLE 6

| Formulation Components | Example 41 | Comparative Example 13 |
|---|---|---|
| Kaurit ™ M70 | 20 | 20 |
| MgCl₂ Cat. for Kaurit ™ M70 | 3 | 3 |
| Blend of fluoroaliphatic carbodiimide and fluoroaliphatic vinyl polymer like Polymers E and X of U.S. Pat. No. 4,215,205 | 11.80 | 23.6 |
| Example 10 product | 11.80 | 0 |
| Water | 953.4 | 953.4 |

The textile used was a 65/35 polyester/cotton fabric specimen. The fabric was dipped into the treatment formulation, passed through a padder, and squeezed so that a wet pick-up of 53% was obtained. The treated fabric specimens were then dried and heat-cured for 3 minutes at 150° C. in an oven. In both examples, a total of 0.375 weight percent fluorochemical solids on fabric were applied. The treated fabric specimens were evaluated for OR, SR, and rain repellency measured by the Bundesmann test. Also the durability towards laundering was tested. The laundering was done in a commercial "Miele" laundering machine, the treated fabric specimens were then dried in a "Miele" tumble dryer, and in some cases, ironed for 15 seconds at 150° C. After this laundering and drying, the OR and SR of the treated fabric specimens were tested again. Test results are listed in Table 7.

TABLE 7

| | Initial Repellency | | Bundesmann Rating at Indicated Time | | | Bundesmann Amount of H₂O | Repellency after Laundering | | | |
|---|---|---|---|---|---|---|---|---|---|---|
| | | | | | | | Tumble Dried | | Ironed | |
| Ex. No. | OR | SR | 1 min. | 5 min. | 10 min. | Penetrated, ml. | OR | SR | OR | SR |
| 41 | 6 | 100 | 5 | 5 | 4+ | 10 | 4 | 80 | 6 | 100 |
| Comp. Ex. 13 | 4 | 100 | 2 | 1 | 1 | 29 | 1 | 0 | 2 | 80 |

The data of Table 7 shows that the fluoroaliphatic-hydrocarbon dimer acids ester product significantly enhances the repellency-imparting properties of the polymer blend of U.S. Pat. No. 4,215,205, particularly the durability of such repellency after laundering and the Bundesmann test ratings.

Various modifications and alterations of this invention will become apparent to those skilled in the art without departing from the scope and spirit of this invention.

We claim:

1. An article comprising a substrate having at least a portion of at least one surface thereof treated with a fluorochemical composition having an acid value of from 0 to about 20, comprising a mixture of normally solid compounds which are fluoroaliphatic esters of dimer acids and/or trimer acids, each of the compounds having at least two fluoroaliphatic groups and a hydrocarbon moiety of at least 30 carbon atoms or having at least one fluoroaliphatic group and a plurality of said hydrocarbon moiety; to impart water and oil repellency thereto.

2. The article of claim 1 wherein said substrate is textile fabric, paper, carpet, leather or stone.

3. The article of claim 2 wherein said substrate is leather.

4. The article of claim 2 wherein said substrate is textile fabric.

5. The article of claim 1 wherein said hydrocarbon moiety comprises a monocycloaliphatic moiety with 6 ring carbon atoms or a bicycloaliphatic moiety with 10 ring carbon atoms.

6. The article of claim 1 wherein said mixture comprises said compounds which are fluoroaliphatic esters of dimer acids.

7. The article of claim 1 wherein said fluorochemical composition comprises a mixture of fluorochemicals represented by $(R_f-L-P)_n-A$ and/or $\{(R_f-L-P)_n-A-P\}_m-Z$ wherein $R_f$ represents a fluoroaliphatic group;

L represents a covalent bond or an organic moiety that optionally contains oxygen-, nitrogen-, or sulfur-containing groups or a combination thereof;

A represents an aliphatic moiety with at least 30 carbon atoms;

P represents a carbonyloxy or oxycarbonyl moiety;

Z represents a mono- or multi-valent hydrocarbon or fluorocarbon moiety;

n represents an integer of about 2 to 10;

n' represents an integer of about 1 to 10;

m represents an integer of about 1 to 5.

8. The article of claim 7 wherein A has 30 to 170 carbon atoms.

9. The articles of claim 7 wherein A has 51 carbon atoms.

10. The article of claim 7 wherein A has 34 carbon atoms.

11. The article of claim 7 wherein n is 3.

12. The article of claim 7 wherein $R_f$ is a perfluorinated aliphatic group of formula $C_xF_{2x+1}$ and x is at least 3.

13. The article of claim 7 wherein L is alkylene, sulfonamido or sulfonamidoalkylene.

14. The article of claim 7 wherein the aliphatic moiety A is derived from a polymerized fatty acid prepared from unsaturated fatty acids selected from the group consisting of palmitoleic acid, linoleic acid, linolenic acid, oleic acid, ricinoleic acid, gadoleic acid, erucic acid, or mixtures thereof.

15. The article of claim 7 wherein said mixture comprises a mixture of esters made from fully esterifying dimer acids with N-methyl-perfluorooctylsulfonamidoethyl alcohol.

16. A method for imparting water and oil repellency to a substrate comprising the step of treating at least a portion of at least one surface of said substrate with a fluorochemical composition having an acid value of from 0 to about 20, comprising a mixture of normally solid compounds which are fluoroaliphatic esters of dimer acids and/or trimer acids, each of the compounds having at least two fluoroaliphatic groups and a hydrocarbon moiety of at least 30 carbon atoms or having at least one fluoroaliphatic group and a plurality of said hydrocarbon moiety.

17. The method of claim 16 wherein said substrate is textile fabric, paper, carpet, leather, or stone.

* * * * *

UNITED STATES PATENT AND TRADEMARK OFFICE
CERTIFICATE OF CORRECTION

PATENT NO. : 6,171,983 B1
DATED : January 9, 2001
INVENTOR(S) : Dirk M. Coppens and Richard J. Grant It is certified that error appears in the above-identified patent and that said Letters Patent is hereby corrected as shown below:

Column 2,
Lines 53 and 59, "diner" should read -- dimer --;

Column 3,
Line 3, "diner" should read -- dimer --;

Column 4,
Line 4, "$[(R_f-L-P)_n-A-P]_mZ$" should read -- $[(R_f-L-P)_{n'}-A-P]_mZ$ --;
Line 51, "and R'" should read -- and R" --;
Line 55, "$CON(R') (CH_2)_k-$" should read -- $-CON(R') (CH_2)_k-$ --;
Line 56, "$(CH_2)_k-$" should read -- $-(CH_2)_k-$ --;
Line 59, "$CH_2CH(OR")CH_2$" should read -- $-CH_2CH(OR")CH_2-$ --;
Line 61, "$CH_2-_kS-$" should read -- $-(CH_2)_kS-$ --;

Column 5,
Line 65, "$(-C\overset{O}{\overset{\|}{S}}-),$" should read -- $(-C\overset{O}{\overset{\|}{S}}-),$ --;

Column 7,
Line 60, "$(R_f-L-OCNH-T-NHC\overset{O}{\overset{\|}{N}}H)_n-A$" should read -- $(R_f-L-O\overset{O}{\overset{\|}{C}}NH-T-NHC\overset{O}{\overset{\|}{N}}H)_n-A$ --;

Column 9,
Line 9, "m is to 4," should read -- m is 1 to 4, --;
Line 26, "$HO-OH_2C(CH_2SCH_2CH_2R_f)_2CH_2OH$" should read -- $HO-CH_2C(CH_2SCH_2CH_2R_f)_2CH_2OH$ --;

Column 10,
Line 23, "diner," should read -- dimer --;

Column 12,
Line 13, insert the Table title -- Standard Test Liquids --;

Column 13,
Line 64, "predispersion" should read -- pre-dispersion --;

UNITED STATES PATENT AND TRADEMARK OFFICE
CERTIFICATE OF CORRECTION

PATENT NO.    : 6,171,983 B1
DATED         : January 9, 2001
INVENTOR(S)   : Dirk M. Coppens and Richard J. Grant It is certified that error appears in the above-identified patent and that said Letters Patent is hereby corrected as shown below:

Column 14,
Line 65, "stirrer,. a reflux" should read -- stirrer, a reflux --;

Column 16,
Line 34, "acid,,the" should read -- acid, the --;

Column 17,
Lines 10 and 11, "Comparative Example 4" should read -- Comparative Example 6 --;
Line 65, "used" should read -- used: --;

Column 18,
Line 17, "30    1.6" should read -- "30  0.6" --;
Line 28, "Penetrator" should read -- Penetrometer --;

Column 19,
Line 64, "a-similar" should read -- a similar --;

Column 21,
Line 12, "$\{(R_f\text{---}L\text{---}P)_n\text{---}A\text{---}P\}_m\text{---}Z$" should read -- $\{(R_F\text{---}L\text{---}P)_n'\text{---}A\text{---}P\}_m\text{---}Z$ --;
Line 16, "contains oxygen --. nitrogen -," should read -- contains oxygen -, nitrogen-, --;

Column 22,
Line 4, "$C_xF_{2+1}$" should read -- $C_xF_{2x+1}$ --;

Signed and Sealed this

Eighth Day of October, 2002

*Attest:*

*Attesting Officer*

JAMES E. ROGAN
*Director of the United States Patent and Trademark Office*